(12) United States Patent
Ishigaki

(10) Patent No.: US 9,250,198 B2
(45) Date of Patent: Feb. 2, 2016

(54) BOARD INSPECTION APPARATUS

(75) Inventor: Hiroyuki Ishigaki, Komaki (JP)

(73) Assignee: CKD Corporation, Aichi (JP)

(*) Notice: Subject to any disclaimer, the term of this patent is extended or adjusted under 35 U.S.C. 154(b) by 737 days.

(21) Appl. No.: 13/458,241

(22) Filed: Apr. 27, 2012

(65) Prior Publication Data

US 2013/0044204 A1 Feb. 21, 2013

(30) Foreign Application Priority Data

Aug. 16, 2011 (JP) ................... 2011-177797

(51) Int. Cl.
H04N 7/18 (2006.01)
G01N 21/956 (2006.01)
H05K 3/34 (2006.01)

(52) U.S. Cl.
CPC .............. G01N 21/95684 (2013.01); G01N 2021/95638 (2013.01); H05K 3/3436 (2013.01); H05K 3/3484 (2013.01)

(58) Field of Classification Search
None
See application file for complete search history.

(56) References Cited

U.S. PATENT DOCUMENTS

| 6,944,521 | B2* | 9/2005 | Yoshida et al. | 700/169 |
| 7,019,826 | B2* | 3/2006 | Vook et al. | 356/237.1 |
| 7,024,031 | B1* | 4/2006 | Castellanos-Nolasco et al. | 382/141 |
| 2009/0315988 | A1* | 12/2009 | Fukazawa | 348/126 |

FOREIGN PATENT DOCUMENTS

JP 2002/228597 A 8/2002
JP 2005-140584 A 6/2005

* cited by examiner

Primary Examiner — Tung Vo
Assistant Examiner — Zaihan Jiang
(74) Attorney, Agent, or Firm — Osha Liang LLP

(57) ABSTRACT

A board inspection apparatus includes an irradiation unit, an imaging unit, and an image processing unit. The image processing unit includes a three-dimensional measurement unit configured to perform three-dimensional measurement of the surfaces of the solder and the resist film by a certain three-dimensional measurement method based on the image data, a virtual standard surface setting unit configured to set a virtual standard surface corresponding to a contacting surface of a certain component mounted in a certain area of the printed board, a protrusion amount calculation unit configured to calculate a protrusion amount from the virtual standard surface for each solder printed and formed in the certain area, and a determination unit configured to determine whether the printed state of the solder passes or fails based on each of the protrusion amounts of the solder.

4 Claims, 7 Drawing Sheets

BOARD INSPECTION APPARATUS

CROSS-REFERENCE TO RELATED APPLICATIONS

This application claims priority to Japanese Patent Application No. 2011-177797 filed on Aug. 16, 2011, the entire contents of which are hereby incorporated by reference.

BACKGROUND OF INVENTION

1. Field of the Invention

The present invention relates to a board inspection apparatus for inspection of condition of solder that has been printed or the like on a printed board.

2. Background Art

Generally, a printed board is equipped with an electrode pattern on a base board formed from glass epoxy resin, and the surface of the printed board is protected by a resist film. When electronic components are mounted on the above mentioned printed board, firstly, cream solder is printed at certain positions on the electrode pattern that are not protected by resist film. Thereafter, the electronic components are temporarily fixed to the printed board by use of viscosity of the cream solder. The above-mentioned printed board is conveyed to a reflow furnace, the printed board is subjected to a certain reflow step, and soldering is performed. In recent years, the printed condition of the cream solder has been inspected at a stage prior the printed board being conveyed to the reflow furnace. During this inspection, a pass-fail determination is made of the printed condition of the solder based on height or the like of the cream solder as measured by a three-dimensional measurement apparatus.

For example, a three-dimensional measurement apparatus that uses the phase shift method uses an irradiation means to irradiate on an object (i.e., the printed board in this case) an optical pattern having a striped light intensity distribution using visible light as the light source. Then, the object is imaged by a CCD camera, and by analysis of the phase differences of the fringes of the above mentioned optical pattern based on the obtained image, three-dimensional shape, and especially height, of the cream solder or the like is measured.

Then, a pass-fail determination is made for the solder based on the volume or the like of the solder calculated taking average height of the resist as a standard height (e.g., see Patent Document 1), or a pass-fail determination is made for the solder based on height of the solder calculated taking height of the surface of the resist as a standard height (e.g., see Patent Document 2).

Patent Document 1: Japanese Unexamined Laid-open Patent Application No. 2002-228597

Patent Document 2: Japanese Unexamined Laid-open Patent Application No. 2005-140584.

However, when the solder is inspected based on average height of the resist film, it is possible that defective solder may be determined as passing due to an inability to sufficiently ensure actual bonding ability with the electronic components despite there being a sufficient amount of solder protruding from the standard position (i.e., average height position).

For example, as shown in FIG. 9(a), among multiple solders 82a through 82f on a printed board and existing in the mounting area of a certain electronic component 80, solders 82a and 82f may exist in regions where the surface height 83a of the resin film 83 is high. Thus, the amount of protrusion of the above mentioned solders 82a and 82f from the peripheral resist film 83 is insufficient, and when the electronic component 80 is actually mounted, the amount that the solder is pressed down by the various electrodes (referred to below as the crush amount) becomes small. A printed board that should normally be determined to have failed due to inadequate connections, may be mistakenly determined to be a non-defective because there was a sufficient amount of protrusion from the average height position Kx of the resist film 83.

In a similar manner, when inspection of this solder is performed using height of the resist film at the periphery of the solder as the standard height, despite there being a sufficient amount of protrusion from the standard position (i.e., surface height position of the resist film), a printed board may be mistaken determined as non-defective even though actual bonding to electronic components can not be sufficiently secured.

For example, as shown in FIG. 9(b), among multiple solders 92a through 92f on a printed board 91 and existing in the mounting area of a certain electronic component 90, solders 92c and 92d may be present in a region of low surface height 93a of the resist film 93. During lowering of the electronic component 90 onto the printed board 91 for mounting, the electronic component 90 contacts the high positions of surface height 93a of the resist film 93 (see the dashed-to-dotted line image of FIG. 9(b)), and the electronic component 90 does not approach the printed board 91 any further. As a result, the crush amounts of the solders 92c and 92d become low, and thus a printed board that should normally be determined to be defective due to inadequate bonding, may be mistakenly determined to be a non-defective since there was a sufficient amount of protrusion from the surface height 93a of the resist film 93.

The above described failures can similarly occur even when co-planarity is inspected.

SUMMARY OF INVENTION

In consideration of the above circumstances, one object of the present invention is to provide a board inspection apparatus that is capable of improvement of accuracy of inspection. Various embodiments of the claimed invention for addressing the above issue will be explained separately below. As may be required, the characteristic operational effects of the embodiments will also be described.

A first embodiment of the claimed invention is directed to a board inspection apparatus for inspection of a printed board having a base board onto which various types of electrodes are formed, the base board surface being protected by a resist film, and solder having been printed onto the base board for connection of various types of components to the electrodes. The board inspection apparatus includes an irradiation unit configured to irradiate a light for three-dimensional measurement onto a surface of the printed board, an imaging unit configured to image a reflected light from the printed board irradiated by the light, and an image processing unit configured to perform at least inspection of the printed board based on an image data obtained by the imaging unit. The image processing unit includes a three-dimensional measurement unit configured to perform three-dimensional measurement of the surfaces of the solder and the resist film by a certain three-dimensional measurement method based on the image data, a virtual standard surface setting unit configured to set a virtual standard surface corresponding to a contacting surface of a certain component mounted in a certain area of the printed board, a protrusion amount calculation unit configured to calculate a protrusion amount from the virtual standard surface for each solder printed and formed in the certain area, and a determination unit configured to determine whether the printed state of the solder passes or fails based on each of the protrusion amounts of the solder.

According to the first embodiment of the claimed invention, the solder and resist film are measured three-dimensionally, and a virtual standard surface is set that corresponds to the contact surface of a certain component that is mounted in a certain area of the printed board. Then, the protrusion amount of each solder from this virtual standard surface is calculated, and based on this protrusion amount, a pass-fail determination is made of the printed state of this solder.

Bonding ability between the component and the solder (bonding strength) is thought to be proportional to the crush amount of the solder during mounting by pressing of the component against the solder (provisional mounting). Therefore, according to the above embodiments, a virtual standard surface is established that resembles the bonding face of a certain component that bonds to each of the solders printed in a certain area, and pass-fail of the printed state (bonding ability of the component) of this solder is checked based on a determination of whether or not the crush amount of the solder at the time of component mounting (e.g. amount of protrusion of the solder from the virtual standard surface) is adequate.

The expression "bonding face of the component" here is taken to mean the plane passing through the tip parts of multiple electrodes protruding from, or exposed at, the package of the component. For example, in the case of a land grid array (LGA) 71 on which planar electrode pads 71b are arrayed in a matrix pattern on the bottom face of a rectangular shaped package 71a as shown in FIG. 8(a), the plane 71c passing through the tip parts of the multiple planar electrode pads 71b becomes the bonding face. Similarly, in the case of a ball grid array (BGA) 72 on which hemispherical electrodes 72b are arrayed in a matrix pattern on the bottom face of a rectangular shaped package 72a as shown in FIG. 8(b), the bonding face becomes the plane 72c passing through the tip parts of the multiple electrodes 72b. In the case of a small outline package (SOP) and Quad Flat Package (QFP) 73 in which electrodes 73b extend from 2 sides or 4 sides of a rectangular shaped package 73a as shown in FIG. 8(c), the plane 73c passing through the tip parts of the multiple electrode tips 73b becomes the bonding face.

As a result, it is possible for there to be less concern that a board having an inappropriate solder crush amount at the time of component mounting would erroneously be determined to be a non-defective product as would happen during conventional component mounting, and it is possible to greatly improve the accuracy of inspection.

A second embodiment of the claimed invention is also directed to a board inspection apparatus for inspection of a printed board having a base board onto which various types of electrodes are formed, the base board surface being protected by a resist film, and solder having been printed onto the base board for connection of various types of components to the electrodes. In the second embodiment, the board inspection apparatus includes an irradiation unit configured to irradiate a light for three-dimensional measurement onto a surface of the printed board, an imaging unit capable of imaging a reflected light from the printed board irradiated by the light, and an image processing unit configured to perform at least inspection of the printed board based on an image data obtained by the imaging unit where the image processing unit includes a three-dimensional measurement unit for performing three-dimensional measurement of the surfaces of the solder and the resist film by a certain three-dimensional measurement method based on the image data, a first virtual standard surface setting unit for setting as a first virtual standard surface a certain surface calculated based on positional information of a highest point of each solder printed in a certain area of the printed board corresponding a certain component, a second virtual standard surface setting unit for setting as a second virtual standard surface a surface obtained by lowering the first virtual standard surface downward to a certain position along a direction orthogonal to the surface of the base board, a protrusion amount calculation unit for calculation of a protrusion amount from the second virtual standard surface for each solder, and a determination unit for determining whether the printed state of the solder passes or fails based on each of the protrusion amounts of the solder.

According to the second embodiment of the claimed invention, the solder and resist film are measured three-dimensionally, and a certain plane calculated based on positional information of the highest point of each of the solders is established as a first virtual standard surface. Furthermore, a second virtual standard surface is established by lowering the above described first virtual standard surface downward to a certain position along a direction orthogonal to the surface of the base board. Then, the protrusion amount (height, volume, or the like) of each solder from this second virtual standard surface is calculated, and based on this protrusion amount, a pass-fail determination is made of the printed state of this solder.

That is, according to the second embodiment of the claimed invention, in a manner similar to that of the previously described embodiments, a virtual standard surface is established that resembles a certain bonding face of the component that bonds to each of the solders printed in a certain area. Then, a pass-fail check is performed of the printed state (bonding ability of the component) of this solder based on a determination of whether of not the crush amount of the solder at the time of component mounting (e.g. amount of protrusion of solder from the second virtual standard surface) is appropriate.

As a result, it is possible for there to be less concern that a board having an inappropriate solder crush amount at the time of component mounting would erroneously be determined to be a non-defective product as would happen during conventional component mounting, and it is possible to greatly improve the accuracy of inspection.

Each component is normally mounted such that the bonding face is horizontal. However, due to size of the component, the number of electrodes, or the like, the bonding face of the component may tilt upward along the upper tip parts of the various solders (highest points) during actual mounting, and the component may be pressed down and attached in this tilted state. For example, when the component is relatively large in comparison to a nozzle used for holding the component by suction during component mounting, the bonding face of the component readily becomes tilted along the upper tip parts of the various solders. In this case, the crush amounts of each of the solders change relative to the case in which the bonding face becomes horizontal.

According to the second embodiment of the claimed invention, a first virtual standard surface is established based on positional information of respective the highest points of the various solders printed in a certain area corresponding to a certain component, and it is possible to more accurately calculated the solder crush amount due to establishing as the second standard surface a plane formed by simply lowering the first virtual standard surface.

Various methods will be considered here for calculation of the first virtual standard surface. The method for establishing the first virtual standard surface is exemplified by setting the first virtual standard surface as a plane passing through the greatest number of highest points of the various solders printed in a certain area corresponding to a certain component, a plane calculated by the least squares method based on the highest points of the various solders, a horizontal plane passing through the average position of the highest positions of the highest points of the various solders, a horizontal plane passing through the highest position among the highest points of the various solders, or the like.

Similarly, various methods have been considered for calculation of the second virtual standard surface. Methods for establishment of the second virtual standard surface are exemplified by use of, as the second virtual standard surface, a plane obtained by lowering the first virtual standard surface down to a position where there is contact with the highest point of the resist film, a plane obtained by lowering the first virtual standard surface until the first virtual standard surface reaches a position above the highest point of the resist film by a certain amount, a plane obtained by lowering the first virtual standard surface by just a certain previously set amount, or the like.

A third embodiment of the claimed invention is the board inspection apparatus according to the second embodiment, where the first virtual standard surface set by the first virtual standard surface setting unit includes a surface that is tilted with respect to the surface of the base board.

As mentioned above, there are cases in which the component is pressed down and attached while the bonding face of the component remains tilting along the upper tip parts of the various solders during mounting. According to the third embodiment of the claimed invention, this type of case has been considered, it is possible to calculate the crush amount of the solder more accurately, and it is possible to further improve the accuracy of inspection.

A fourth embodiment of the claimed invention is the board inspection apparatus according to any one of the first through the third embodiments of the claimed invention, where the determination unit determines, based on a previously set upper value and a previously set lower value, whether the printed state of the solder passes or fails based on a determination of whether or not the protrusion amount of each of the solders is within a permissible range.

According to the fourth embodiment of the claimed invention, not only when it is not possible to sufficiently secure bonding ability with the component because the crush amount of the solder is excessively small during mounting of the component, but also, when shorts or the like are caused by an excessively large crush amount of the solder, it is possible to detect the problems. As a result, it is possible to further improve accuracy of inspection.

Other aspects and advantages of the invention will be apparent from the following description and the appended claims.

DETAILED DESCRIPTION

One or more embodiments of the claimed invention are explained below while referring to figures.

Figure 2:
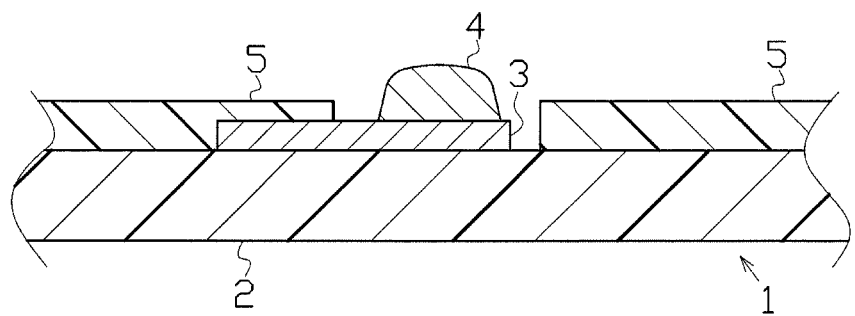
FIG. 2 is a partial cross-sectional drawing of a printed board according to one or more embodiments of the claimed invention.

As shown in FIG. 2, the printed board 1 is equipped with an electrode pattern 3 formed from copper foil on a base board 2, which is formed from glass epoxy resin or the like and has a flat plate shape (i.e., provided with a flat surface). Cream solder 4 is printed on a certain electrode pattern 3.

The printed board 1 is coated by a semi-transparent resist film 5 so that the cream solder 4 is only carried on the printed board 1 at a certain part of the wiring of the electrode pattern 3.

Figure 1:
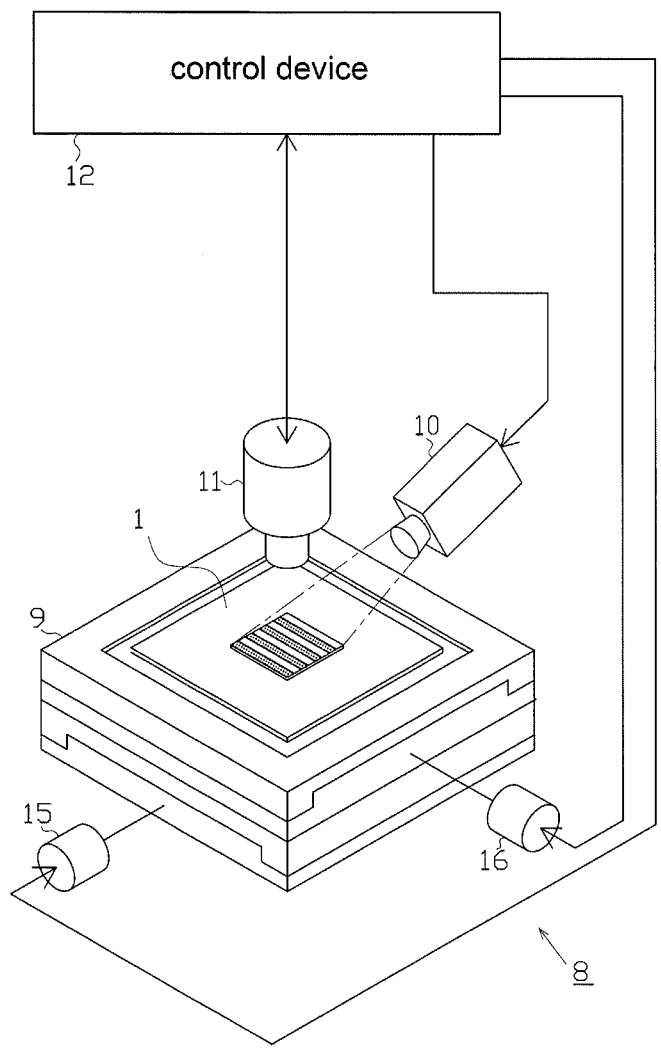
FIG. 1 is a schematic tilted-perspective view of a board inspection apparatus according to one or more embodiments of the claimed invention.

FIG. 1 is a schematic structural drawing of the board inspection apparatus 8 of the present embodiment equipped with a three-dimensional measurement apparatus. As shown in this drawing, the board inspection apparatus 8 includes: a carrying stage 9 for carrying the printed board 1, an irradiation device 10 as an irradiation unit for irradiating a certain light component pattern from above at a tilted angle relative to the surface of the printed board 1, and a CCD camera 11 as an imaging unit for imaging a part that is irradiated on the printed board 1, and a control device 12 as a control unit for performing image processing, calculation processing, and various types of control within the board inspection apparatus 8.

Motors 15 and 16 are arranged at the above described carrying stage 9, and due to drive control of these motors 15 and 16 by the control device 12, the printed board 1 carried on the carrying stage 9 can be slid in an arbitrary direction (i.e., x axis direction and y axis direction).

Figure 3:
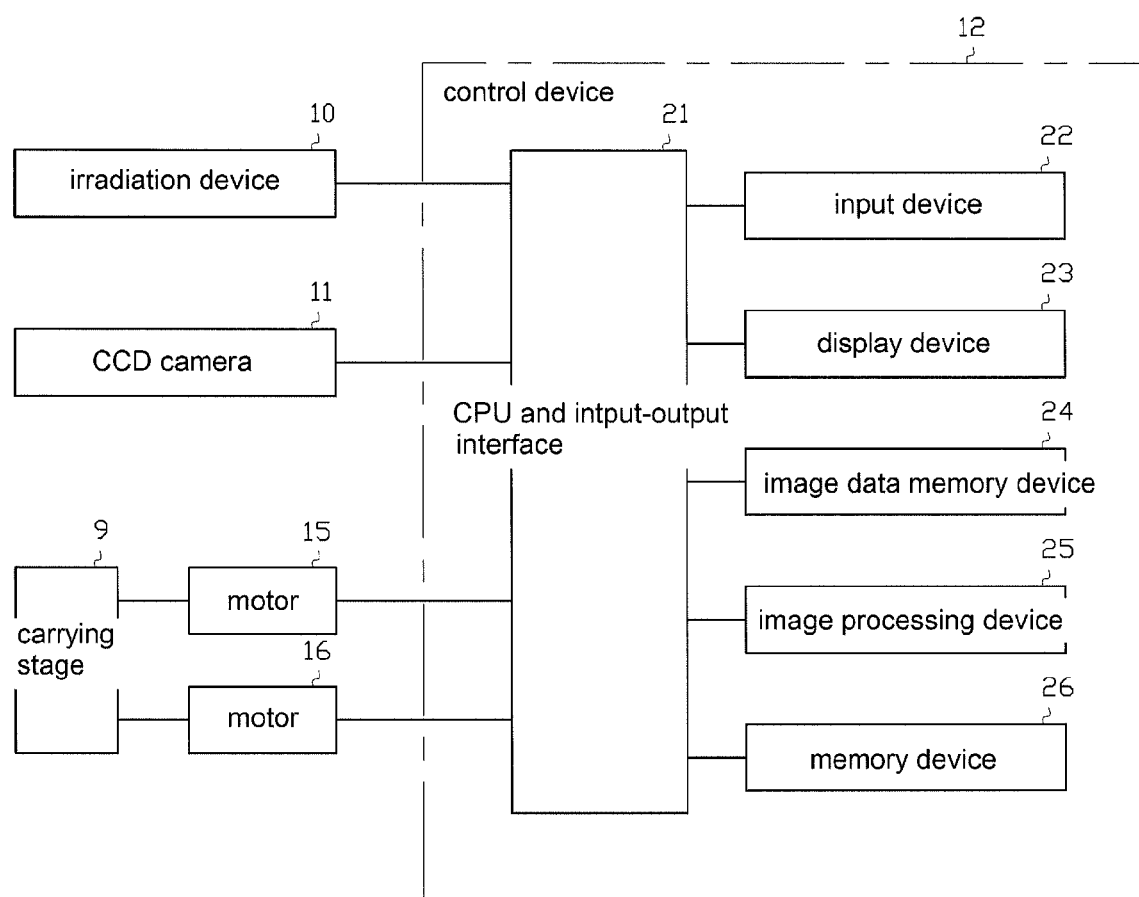
FIG. 3 is a block diagram for providing a summary of the board inspection apparatus.

The electrical configuration of the control device 12 will be explained next. As shown in FIG. 3, the control device 12 is equipped with: a CPU and input-output interface 21 for performing overall control of the board inspection apparatus 8; an input device 22 constituted by a keyboard, mouse, or touch panel; a display device 23 that has a CRT, liquid crystal display, or the like display screen; an image data memory device 24 for memory of image data or the like based on imaging by the CCD camera 11; an image processing device 25 as an image processing unit for measurement of height or volume of the cream solder 4 based on imaging by the CCD camera 11; and a memory device 26 as a memory unit for memory of design data, inspection results, or the like. Furthermore, each of these devices 22 through 26 is electrically connected to the CPU and the input-output interface 21.

Figure 4:
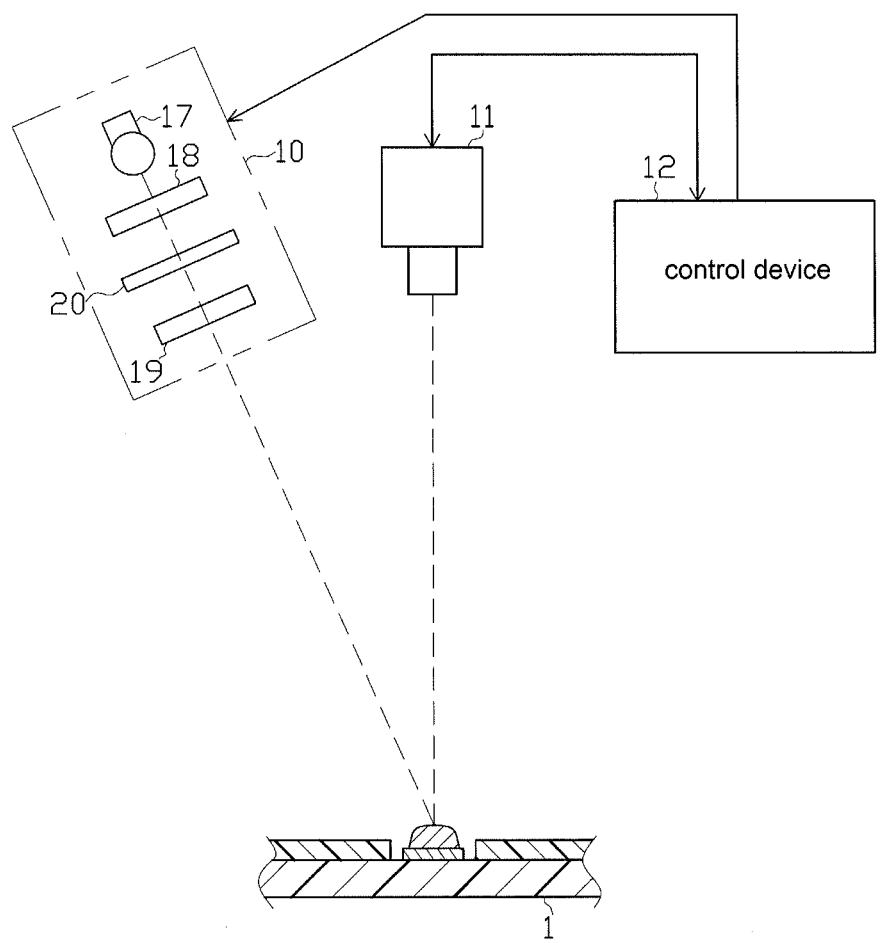
FIG. 4 is a schematic drawing showing the board inspection apparatus according to one or more embodiments of the claimed invention.

As shown in FIG. 4, the irradiation device 10 has a light source 17, a condenser lens 18 for collecting light from the light source 17, an irradiation lens 19, and a liquid crystal optical shutter 20 disposed between the condenser lens 18 and the irradiation lens 19. Light from the light source 17 passes through the liquid crystal optical shutter 20 and is irradiated upon the printed board 1 so that a stripe-shaped optical pattern having sinusoidally varying brightness is irradiated onto the printed board 1. The liquid crystal optical shutter 20 is configured to cause change of the phase of the above described optical pattern in increments of a certain pitch.

Figure 5:
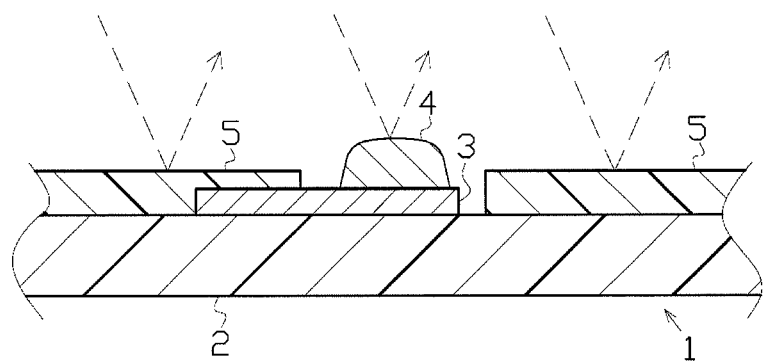
FIG. 5 is a schematic drawing for explanation of the reflection at the printed board of light irradiated from an irradiation device in one or more embodiments of the claimed invention.

As shown in FIG. 5, wavelength of the radiating light from the above described light source 17 is set such that that there is reflection also from the surface of the resist film 5 rather than just from the surface of the cream solder 4. However, in the present embodiment, the light source 17 irradiates ultraviolet radiation by use, for example, of a LED, UV lamp, or the like. Light of a relatively short wavelength, such as ultraviolet radiation, readily reflects from surfaces, and so it becomes possible to more reliably cause reflection from the surface of a semi-transparent object such as a resist film 5. The condenser lens 18 and the irradiation lens 19 are capable of transmitting light of the above described wavelength, and the CCD camera 1 is capable of imaging only ultraviolet radiation.

The inspection procedure using the board inspection apparatus 8 will be explained next. Firstly, the printed board 1 is carried on the carrying stage 9, the control device 12 performs drive control of the motors 15 and 16 to cause movement of the printed board 1 to a certain position, and the printed board 1 is moved to an initial position. Surface of the printed board 1 is divided beforehand into areas, each of a unit size that is the same as the size of the field of view of the CCD camera 11, and this initial position, for example, is the position of one of these areas of the printed board 1

Thereafter, the control device 12 causes operation of the irradiation device 10, and irradiation of the optical pattern starts. The irradiated light reflects from the surface of the printed board (i.e., from the cream solder 4, resist film 5, or the like), and this reflected light is imaged by the CCD camera 11. Moreover, phase of the optical pattern at this time, for example, is shifted in increments of one quarter pitch, and the optical pattern is controlled so that there is consecutive switching between 4 types of optical patterns. During irradiation of each of the optical patterns in this manner, the control device 12 controls operation of the CCD camera 11. The inspection area part is imaged for each of these optical patterns, image data are obtained as 4 respective images, and the image data are stored in the image data memory device 24.

Thereafter, various types of image processing are controlled by the control device 12 based on these stored image data. During this image processing, the control device 12 controls and drives the motors 15 and 16 and causes the carrying stage 9 to move to the next inspection area. The control device 12 also stores in the image data memory device 24 the image data from this inspection area. Once image data processing has been completed by the image data memory device 14, because the next image data have been stored already in the image data memory device 24, it is possible for the control device 12 to quickly carry out the next image processing. That is, the inspection includes movement to, and image input at, the next inspection area (i.e., inspection area m+1), and the inspection, on the other hand, includes performance of image processing and comparison determination at the inspection area m. Thereafter, the above-described parallel processing is repeatedly performed alternatingly until completion of inspection of all the inspection areas. In this manner, the board inspection apparatus 8 of the present embodiment is able to quickly and reliably perform inspection of the printed state of cream solder 4 on the printed board 1 by sequential image processing while moving the inspection area based on control by the control device 12.

Figure 6:
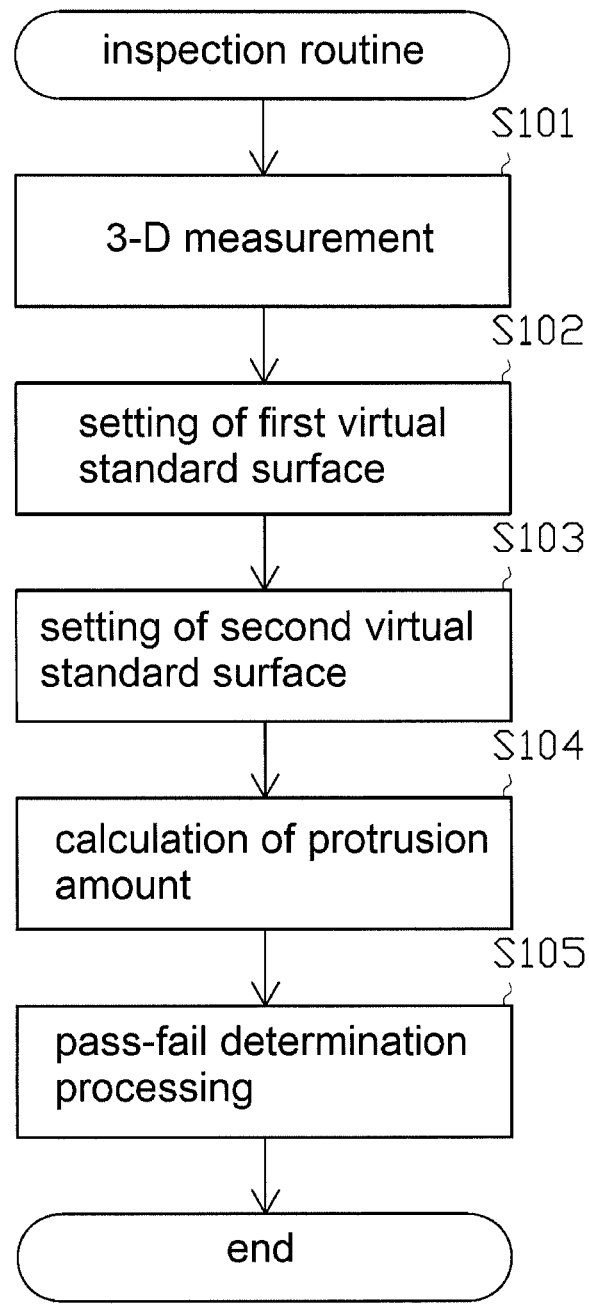
FIG. 6 is a flow chart showing an inspection routine according to one or more embodiments of the claimed invention.
Figure 7A:
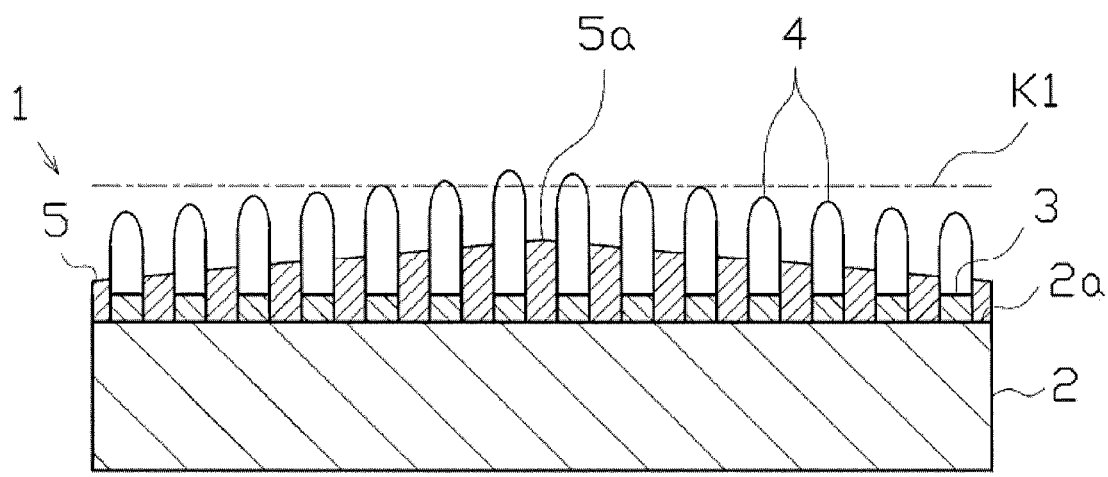
FIGS. 7(a) and 7(b) are schematic drawings for explanation of the process of setting the virtual standard surface in one or more embodiments of the claimed invention.
Figure 7B:
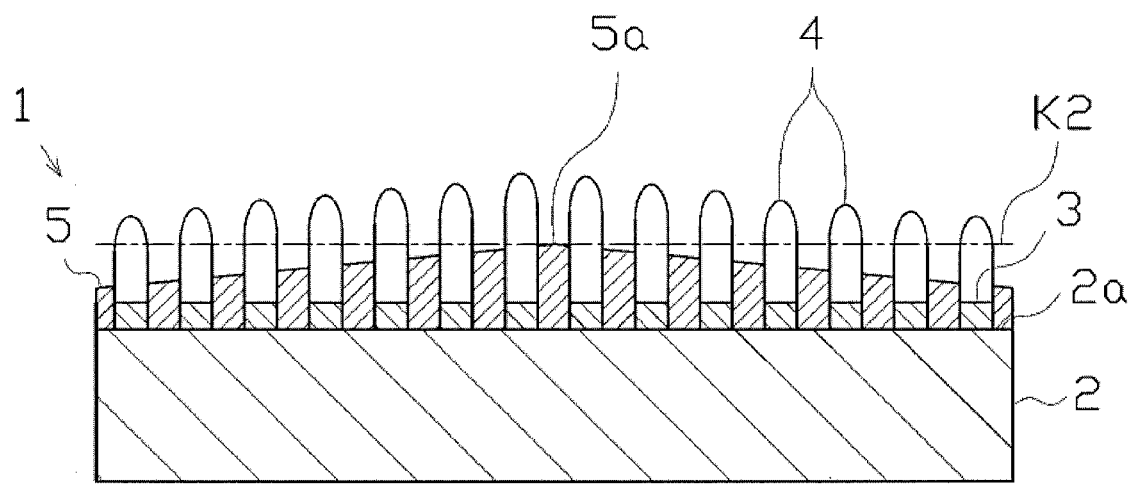

The inspection routine that is performed for each certain area on the printed board 1 (referred to hereinafter as "the mounting area") corresponding to a certain mounted electronic component will be explained in detail while referring to FIGS. 6 and 7. FIG. 6 is a flow chart showing the inspection routine. FIGS. 7(*a*) and (*b*) are schematic drawings for explanation of the process of setting the virtual standard surface.

Figure 8A:
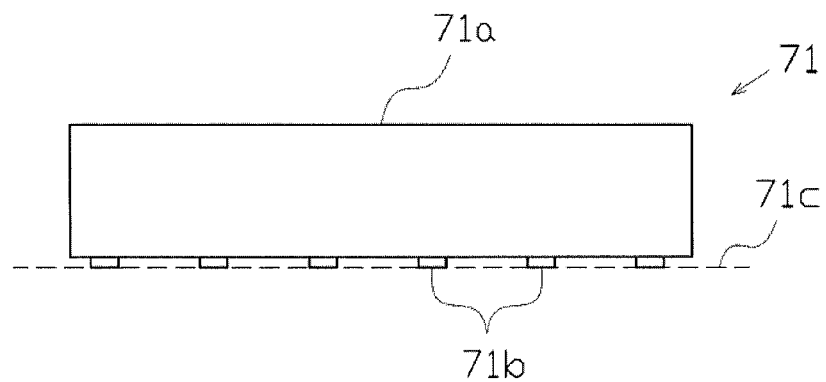
FIGS. 8(a), 8(b), and 8(c) are schematic drawings showing various types of electronic components in one or more embodiments of the claimed invention.
Figure 8B:
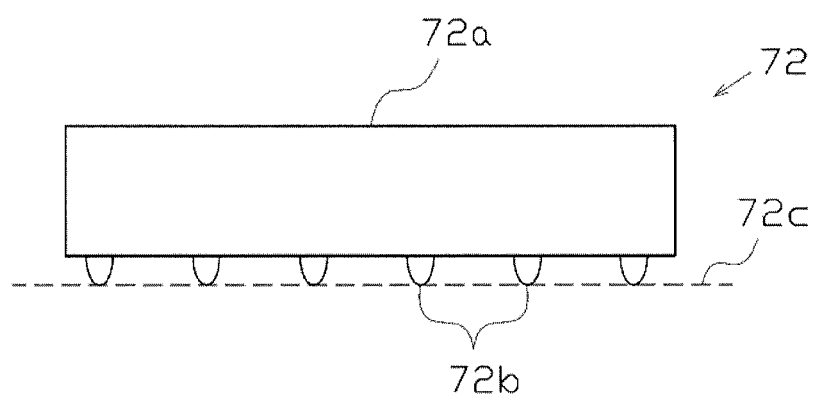
Figure 8C:
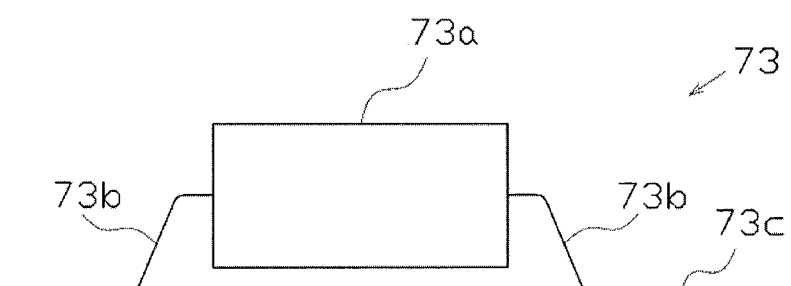
Figure 9A:
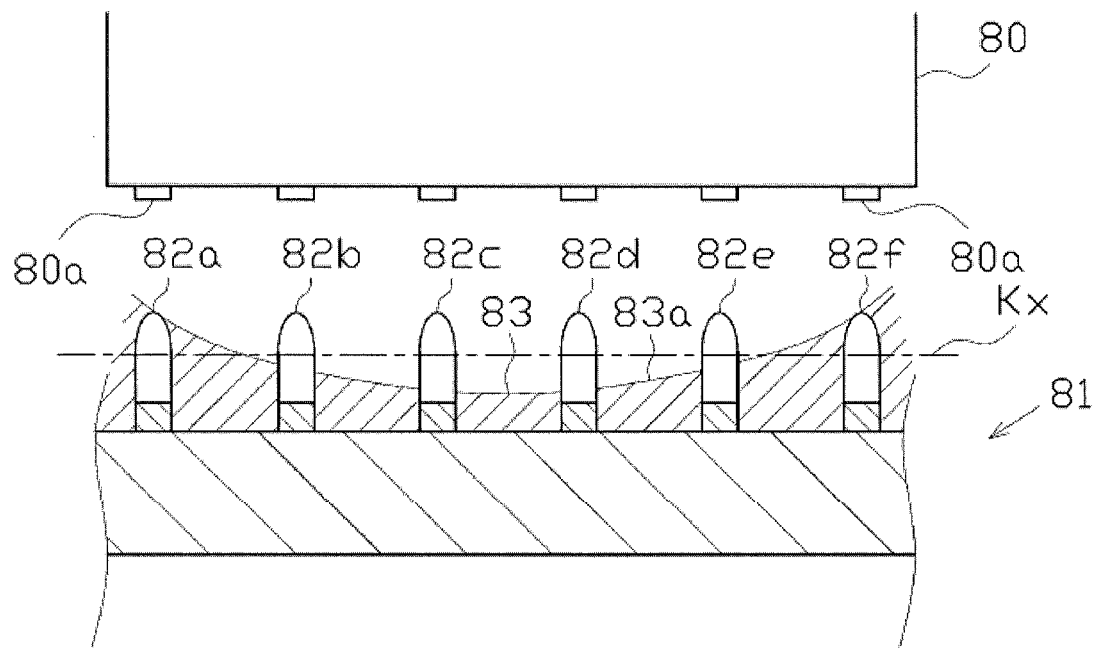
FIGS. 9(a) and 9(b) are schematic drawings for explanation of the conventional inspection process.
Figure 9B:
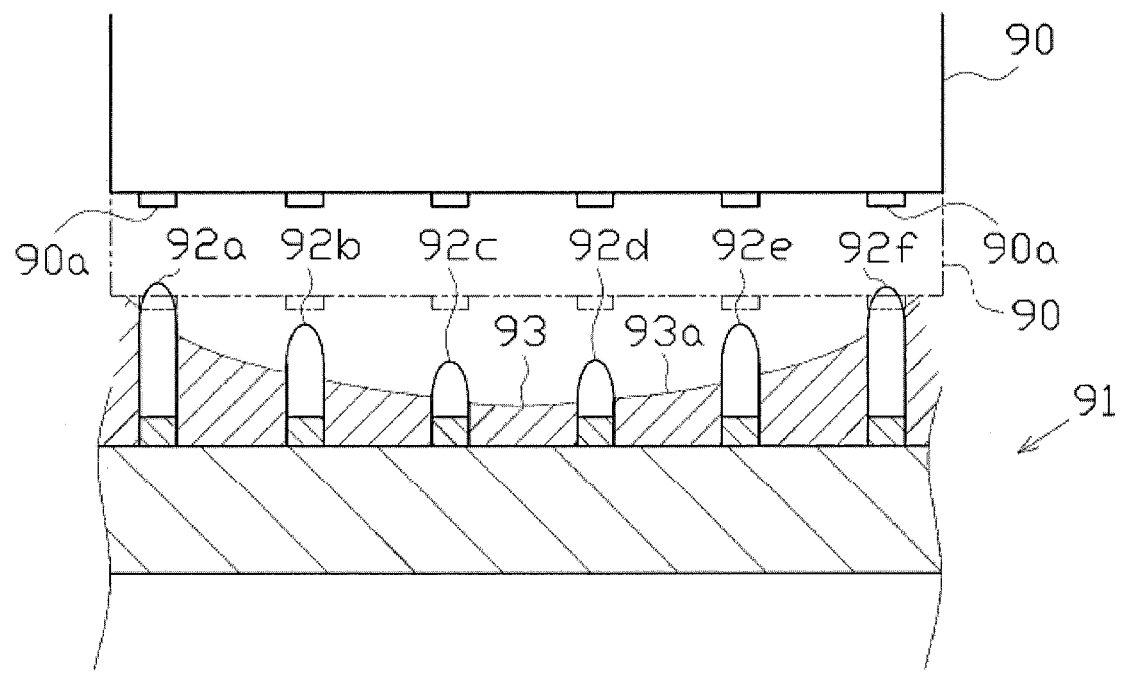

The certain electronic component is exemplified by a land grid array (LGA) having planar electrode pads 71*d* arrayed in a matrix pattern at the bottom face of a rectangular package 71*a* as shown in FIG. 8(*a*), a ball grid array (BGA) 72 having hemispherical electrodes 72*b* arrayed in a matrix pattern at the bottom face of a rectangular package 72*a* as shown in FIG. 8(*b*), a small outline package (SOP) and a quad flat package (QFP) 73 having electrode terminals 73*b* extending from 2 or 4 sides of a rectangular package 73*a* as shown in FIG. 8(*c*), or the like. One or more embodiments of the claimed invention can be used for a printed board 1 on which are mounted electronic components that differ from the above-described electronic components 71 through 73.

In step S101, the control device 12 executes three-dimensional measurement processing. The function for performing this processing is executed by the three-dimensional measurement unit in the present embodiment.

Specifically, the control device 12 (image processing device 25) uses each of the obtained optical pattern image data (i.e., the 4 images) and performs three-dimensional measurement (i.e., height measurement) of the surface of the resist 5 and the cream solder 4 within the mounting area by the widely known phase shift method. The height data obtained during this procedure is stored in the memory device 26.

During step S102, the control device 12 performs processing to set the first virtual standard surface. The function for performing this processing is executed by the three-dimensional measurement unit in the present embodiment.

Specifically, based on the height data stored in the memory device 26, the control device 12 firstly extracts a respective highest point of each cream solder 4 printed in the mounting area. Thereafter, based on the positional information of the highest point of each cream solder 4, the first virtual standard surface K1 (see FIG. 7(*a*)) is calculated and set. The first virtual standard surface K1 in the present embodiment is calculated by the least squares method.

During step S103, the control device 12 executes processing to set the second virtual standard surface. The function for performing this processing is executed by the second virtual standard surface setting unit in the present embodiment.

Specifically, the control device 12 calculates and sets as the second virtual standard surface K2 (see FIG. 7(*b*)) a plane obtained by lowering the above-described first virtual standard surface K1 in a direction orthogonal to the surface 2*a* of the base board 2 (downward direction in FIG. 7). In the present embodiment, a highest point 5*a* of the resist film 5 within the mounting area is extracted, and the second virtual standard surface K2 is set as the plane obtained by lowering the above described first virtual standard surface K1 down to a position at which there is contact with the highest point 5*a*.

During step S104, the control device 12 performs protrusion amount calculation processing. The function for performing this processing is executed by the protrusion amount calculation unit in the present embodiment.

Specifically, the control device 12 (image processing device 25) calculates the protrusion amount (i.e., height, volume, or the like) of each cream solder 4 that protrudes upward from the above described second virtual standard surface K2. The data obtained during this step are stored in the memory device 26.

During step S105, the control device 12 performs pass-fail determination processing for this mounting area, and the present inspection routine terminates. The function for performing this processing is executed by the determination unit in the present embodiment.

Specifically, the control device 12 makes a determination by comparison of the protrusion amount of each cream solder 4 found during the above step S104 with standard data stored beforehand in the memory device 26, and based on a determination of whether or not the results of this comparison are within the permissible range, a pass-fail determination is made for the printed state of each cream solder 4. The inspection results are stored in the memory device 26. Because it is undesirable for the protrusion amount of each cream solder 4 to be excessively small or excessively large, in the present embodiment, the upper and lower limit values are stored as the above-described standard data.

A printed board 1 that has a cream solder 4 that was determined to be defective according to the above inspection routine is ejected by a non-illustrated ejection mechanism positioned downstream of the board inspection apparatus 8 in the board manufacturing line. A printed board 1 that was determined to be non-defective is guided to a non-illustrated component mounting device.

According to the present embodiment as described above, three-dimensional measurement of the surface of the cream solder 4 and the resist film 5 within the mounting area is performed, and a certain plane calculated based on positional information of the highest point of each cream solder 4 is set as the first virtual standard surface K1. Furthermore, the second virtual surface K2 was set by lowering this first virtual standard surface K1 along a direction orthogonal to the surface 2a of the base board 2 down to a certain position. Then, the protrusion amount for each cream solder 4 from this second virtual standard surface K2 is calculated, and a pass-fail determination is made of the printed state of these cream solders 4 based on the calculated result.

Bonding ability (bonding strength) between the cream solders 4 and the mounted electronic component 71 through 73 is thought to be proportional to the crush amount of the cream solder 4 during pressing and mounting of the electronic components 71 through 73 on the cream solder 4. Therefore, in the present embodiment, the virtual standard surfaces K1 and K2 are set to resemble the bonding faces 71c through 73c of certain electronic components 71 through 73, respectively, that bond with the various cream solders printed in the mounting areas. Pass-fail inspection of the printed state (i.e. bonding ability of electronic components 71 through 73) of this cream solder 4 is performed based on a determination of whether or not the crush amount (protrusion amount of the cream solder 4 from the second virtual standard surface K2) of the cream solder 4 during component mounting is appropriate.

As a result, there is decreased concern that a printed board that has an inappropriate crush amount of the cream solder 4 during component mounting would be determined to be non-defective, as would have occurred conventionally, and it is possible to greatly improve the accuracy of inspection.

Normally, the bonding faces 71c through 73c of electronic components 71 through 73, respectively, are mounted horizontally. However, due to the size of the electronic components 71 through 73, the number of electrodes 71b through 73b, or the like, the electronic components 71 through 73 may be pressed down and attached while the bonding faces 71c through 73c of the electronic components 71 through 73 are actually tilted along the positions of the upper tip part (highest point) of each cream solder 4. For example, if the electronic components 71 through 73 are relatively large in comparison to a suction-retaining nozzle that holds these electronic components 71 through 73 during component mounting, the bonding faces 71c through 73c of the electronic components 71 through 73 readily become tilted to follow the upper tip parts of each of the cream solders 4. In this case, the crush amount of each cream solder 4 changes relative to when the bonding faces 71c through 73c were oriented horizontally.

In the present embodiment, the first virtual standard surface K1 is set based on positional information of the highest point for each cream solder 4 printed within the mounting areas corresponding to the certain electronic components 71 through 73, and the second virtual standard surface K2 is set by simply lowering this first virtual standard surface K1. It is thus possible to calculate more accurate crush amounts of the cream solder 4.

The above details of the above-described embodiments are not limiting, and for example, embodiments as described below may be used. Modified examples and examples of other applications not cited below can also be used.

(a) In the present embodiment, a specific example was described of inspection of cream solder 4 printed on the printed board 1. However, this example is not limiting, and the present invention can be used for inspection of solder bumps or the like.

(b) In the above embodiments, ultraviolet radiation was irradiated from the irradiation device 10. However, other light may be used, such as blue light or the like, as long as reflection from the surface of the resist film 5 is possible.

(c) In the above embodiments, a plane that was calculated by the least square's method using the highest points of each of the cream solders 4 was set as the first virtual standard surface K1. However, the method for calculation of the first virtual standard surface K1 is not limited to this method. For example, a plane passing through the maximum number of highest points of each of the cream solders 4 printed in the mounting area corresponding to a certain electronic component, a horizontal plane passing through an average height position of the respective highest point of each of the cream solders 4, a horizontal plane passing through the highest position among the highest points of each of the cream solders 4, or the like may be set as the first virtual standard surface K1.

(d) In the above embodiments, the second virtual standard surface K1 was set at a plane obtained by lowering the first virtual standard surface K1 to a position of contact with the highest point 5a of the resist film 5 within the mounting area. However, the method of calculation of the second virtual standard surface K2 is not limited to this calculation method. For example, a plane obtained by lowering the first virtual standard surface K1 down until a position is reached that is a certain amount above the highest point 5a of the resist film 5, a plane obtained by lowering the first virtual standard surface K1 down by just a previously set certain amount, or the like can be set as the second virtual standard surface K2.

(e) In the above embodiments, a certain plane that was calculated based on positional information of the highest point of each of the cream solders 4 within the mounting area was set as the first virtual standard surface K1, and the second virtual standard surface K2 was set by lowering this first virtual standard surface K1 along a direction orthogonal to the surface 2a of the base board 2 downward to a certain position. In the above embodiments, pass-fail determination of the printed state of these cream solders 4 was based on the protrusion amount of each cream solder 4 from this second virtual standard surface K2.

The above embodiments are not limiting, and, for example, when there is no tilting of the bonding face 71c of the electronic component 71 along the upper tip parts of each of the cream solders 4 during mounting, the first virtual standard surface setting processing of step S102 in the above embodiment may be omitted. In this case, instead of the processing of the above described step S103, for example, a certain horizontal plane is lowered until a position is reached of contact with the highest point 5a of the resist film 5 within the mounting area, and processing is performed to set the resultant plane as the virtual standard surface corresponding to the bonding face 71c of the certain electronic component 71 mounted in this mounting area. The function for performing this processing is executed by the virtual standard surface setting unit in the present embodiment. Then, pass-fail determination of the printed state of these cream solders 4 is performed based on the protrusion amount of each cream solder 4 from this virtual standard surface.

(f) In the above embodiments, the phase shift method was adopted as the three-dimensional measurement method. However, it is possible to utilize various types of three-dimensional measurement such as the light-section method, Moiré method, focusing method, confocal method, spatial code method, lattice fringe projection method, or the like.

(g) In the above embodiment, a configuration was used that determined pass-failure of the printed state of each cream solder 4 based on a determination of whether or not the protrusion amount of each cream solder 4 was within a permissible range according to an upper limit value and lower limit value set as the standard data. However, this configuration is not limiting, and a configuration is permissible in which, for example, either the upper limit value or the lower limit value is set, and a determination is made that the board in non-defective when the protrusion amount for each cream solder 4 is less than or equal to the upper limit value, or is greater than or equal to the lower limit value.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

DESCRIPTION OF REFERENCE CHARACTERS

1 . . . printed board
2 . . . base board
3 . . . electrode pattern
4 . . . cream solder
5 . . . resist film
8 . . . board inspection apparatus
9 . . . carrying stage
10 . . . irradiation device
11 . . . CCD camera
12 . . . control device
24 . . . image data memory device
25 . . . image processing device
26 . . . memory device
K1 . . . first virtual standard surface
K2 . . . second virtual standard surface

What is claimed is:

1. A board inspection apparatus for inspection of a printed board having a base board onto which various types of electrodes are formed, the base board surface being protected by a resist film, and solder having been printed onto the base board for connection of various types of components to the electrodes,
   wherein the board inspection apparatus comprises:
      an irradiation unit configured to irradiate a light for three-dimensional measurement onto a surface of the printed board;
      an imaging unit configured to image a reflected light from the printed board irradiated by the light; and
      an image processing unit configured to perform at least inspection of the printed board based on an image data obtained by the imaging unit,
   wherein the image processing unit comprises:
      a three-dimensional measurement unit configured to perform three-dimensional measurement of the surfaces of the solder and the resist film by a certain three-dimensional measurement method based on the image data;
      a first virtual standard surface setting unit configured to set as a first virtual standard surface a certain surface calculated based on positional information of a highest point of each solder printed in a certain area of the printed board corresponding a certain component;
      a second virtual standard surface setting unit configured to set as a second virtual standard surface a surface obtained by lowering the first virtual standard surface downward to a certain position above the printed board along a direction orthogonal to the surface of the base board;
      a protrusion amount calculation unit configured to calculate a protrusion amount from the second virtual standard surface for each solder; and
      a determination unit configured to determine whether the printed state of the solder passes or fails based on each of the protrusion amounts of the solder.

2. The board inspection apparatus according to claim 1, wherein the first virtual standard surface set by the first virtual standard surface setting unit includes a surface that is tilted with respect to the surface of the base board.

3. The board inspection apparatus according to claim 1, wherein the determination unit determines, based on a previously set upper value and a previously set lower value, whether the printed state of the solder passes or fails based on a determination of whether or not the protrusion amount of each of the solders is within a permissible range.

4. The board inspection apparatus according to claim 2, wherein the determination unit determines, based on a previously set upper value and a previously set lower value, whether the printed state of the solder passes or fails based on a determination of whether or not the protrusion amount of each of the solders is within a permissible range.

* * * * *